United States Patent
Hyde et al.

(10) Patent No.: US 10,512,420 B2
(45) Date of Patent: Dec. 24, 2019

(54) SYSTEMS TO MONITOR BODY PORTIONS FOR INJURY AFTER IMPACT

(71) Applicant: Elwha LLC, Bellevue, WA (US)

(72) Inventors: Roderick A. Hyde, Redmond, WA (US); Jordin T. Kare, Seattle, WA (US); Eric C. Leuthardt, St. Louis, MO (US); Mark A. Malamud, Seattle, WA (US); Tony S. Pan, Bellevue, WA (US); Elizabeth A. Sweeney, Seattle, WA (US); Clarence T. Tegreene, Mercer Island, WA (US); Charles Whitmer, North Bend, WA (US); Lowell L. Wood, Jr., Bellevue, WA (US)

(73) Assignee: ELWHA LLC, Bellevue, WA (US)

( * ) Notice: Subject to any disclaimer, the term of this patent is extended or adjusted under 35 U.S.C. 154(b) by 57 days.

(21) Appl. No.: 14/549,689

(22) Filed: Nov. 21, 2014

(65) Prior Publication Data

US 2016/0143534 A1    May 26, 2016

(51) Int. Cl.
*A61B 5/11* (2006.01)
*A41D 13/12* (2006.01)
(Continued)

(52) U.S. Cl.
CPC ............ *A61B 5/11* (2013.01); *A41D 13/1281* (2013.01); *A42B 3/046* (2013.01); *A61B 5/4041* (2013.01);
(Continued)

(58) Field of Classification Search
CPC ... A61B 5/1036; A61B 5/6802; A61B 5/6804; A61B 5/7275; A61B 5/7282;
(Continued)

(56) References Cited

U.S. PATENT DOCUMENTS 4,554,930 A    11/1985  Kress
4,830,014 A     5/1989  Goodman et al.
(Continued)

FOREIGN PATENT DOCUMENTS

EP          2 587 240 A2    5/2013
WO     WO 2011/084709 A2    7/2011

OTHER PUBLICATIONS

Wang, Y., Wang, L., Yang, T., Li, X., Zang, X., Zhu, M., Wang, K., Wu, D. and Zhu, H. (2014), "Wearable and Highly Sensitive Graphene Strain Sensors for Human Motion Monitoring". Adv. Funct. Mater., 24: 4666-4670.*

(Continued)

*Primary Examiner* — Devin B Henson
(74) *Attorney, Agent, or Firm* — Daniel J. Honz; Advent, LLP

(57) ABSTRACT

Systems are described for monitoring extremities for injury or damage following a physical impact. A device embodiment includes, but is not limited to, a deformable substrate; a sensor assembly coupled to the deformable substrate, the sensor assembly configured to generate one or more sense signals based on detection of a physical impact to a body portion and based on detection of a physiological parameter; circuitry operably coupled to the sensor assembly and configured to receive the one or more sense signals based on detection of the physical impact and to determine whether the physical impact exceeds a threshold impact value, the circuitry configured to instruct the sensor assembly to detect one or more physiological parameters of the body portion when the physical impact exceeds the threshold impact value; and a reporting device operably coupled to the circuitry.

48 Claims, 11 Drawing Sheets

(51) Int. Cl.
*A42B 3/04* (2006.01)
*A61B 5/00* (2006.01)

(52) U.S. Cl.
CPC .......... *A61B 5/6806* (2013.01); *A61B 5/6807* (2013.01); *A61B 5/7282* (2013.01); *A61B 5/7285* (2013.01); *A61B 2562/0219* (2013.01); *A61B 2562/0247* (2013.01); *A61B 2562/0257* (2013.01); *A61B 2562/0266* (2013.01); *A61B 2562/04* (2013.01); *A61B 2562/164* (2013.01); *A63B 2220/53* (2013.01); *A63B 2220/58* (2013.01); *A63B 2220/805* (2013.01)

(58) Field of Classification Search
CPC .... A61B 2562/0247; A61B 2562/0252; A61B 2562/0257; A61B 2562/0261; A61B 2562/164; A61B 5/6814; A61B 5/6843; A61B 5/6844; A61B 2562/0266; A42B 3/046; A63B 2220/53; A63B 2220/58; A63B 2220/806; A41D 13/1281

See application file for complete search history.

(56) References Cited

U.S. PATENT DOCUMENTS

| | | | |
|---|---|---|---|
| 5,368,025 | A | 11/1994 | Young et al. |
| 5,929,332 | A | 7/1999 | Brown |
| 6,195,921 | B1 | 3/2001 | Truong |
| 6,470,199 | B1 | 10/2002 | Kopotic et al. |
| 6,622,034 | B1 | 9/2003 | Gorski et al. |
| 6,771,994 | B2 | 8/2004 | Kiani et al. |
| 6,847,913 | B2 | 1/2005 | Wigley et al. |
| 6,918,883 | B2 | 7/2005 | Horton et al. |
| 7,324,841 | B2 | 1/2008 | Reho et al. |
| 7,377,944 | B2 | 5/2008 | Janusson et al. |
| 7,383,071 | B1 | 6/2008 | Russell et al. |
| 7,716,005 | B2 | 5/2010 | Shoureshi et al. |
| 7,770,473 | B2 | 8/2010 | Von Lilienfeld-toal et al. |
| 8,057,388 | B1 | 11/2011 | Russell et al. |
| 8,111,165 | B2 | 2/2012 | Ortega et al. |
| 8,140,143 | B2 | 3/2012 | Picard et al. |
| 8,253,586 | B1 | 8/2012 | Matak |
| 8,292,830 | B2 | 10/2012 | Bertocci |
| 8,301,258 | B2 | 10/2012 | Chan et al. |
| 8,416,088 | B2 | 4/2013 | Ortega et al. |
| 8,449,471 | B2 | 5/2013 | Tran |
| 2003/0214408 | A1 | 11/2003 | Grajales et al. |
| 2003/0224685 | A1 | 12/2003 | Sharma |
| 2005/0067816 | A1* | 3/2005 | Buckman .............. A41D 13/018 280/730.1 |
| 2007/0038042 | A1 | 2/2007 | Freeman |
| 2007/0206655 | A1 | 9/2007 | Haslett et al. |
| 2009/0112078 | A1 | 4/2009 | Tabe |
| 2009/0254003 | A1 | 10/2009 | Buckman |
| 2011/0218756 | A1 | 9/2011 | Callsen et al. |
| 2011/0257496 | A1 | 10/2011 | Terashima et al. |
| 2012/0304365 | A1 | 12/2012 | Howard et al. |
| 2013/0060168 | A1 | 3/2013 | Chu et al. |
| 2013/0110415 | A1* | 5/2013 | Davis .................... A42B 3/046 702/41 |
| 2013/0125296 | A1* | 5/2013 | Rabinovitch .......... A42B 3/046 2/413 |
| 2013/0137943 | A1 | 5/2013 | Pinto |
| 2013/0160183 | A1 | 6/2013 | Reho |
| 2013/0192071 | A1 | 8/2013 | Esposito et al. |
| 2013/0321168 | A1 | 12/2013 | Mahony |
| 2014/0143940 | A1 | 5/2014 | Iuliano et al. |
| 2014/0159922 | A1* | 6/2014 | Maliszewski ......... A42B 3/046 340/870.16 |
| 2014/0200486 | A1 | 7/2014 | Bechtel et al. |
| 2014/0266752 | A1* | 9/2014 | John .................... A61B 5/1117 340/665 |
| 2015/0173666 | A1* | 6/2015 | Smith .................... A61B 5/11 600/301 |
| 2015/0173669 | A1* | 6/2015 | Simon ................ G06F 19/3431 600/595 |
| 2015/0351690 | A1* | 12/2015 | Toth .................... A61B 5/6833 600/373 |

OTHER PUBLICATIONS

Kim et al., "Epidermal Electronics", Science, Aug. 12, 2011, vol. 33, Issue 6044, pp. 838-843.*
Yeo, W.-H., Kim, Y.-S., Lee, J., Ameen, A., Shi, L., Li, M., Wang, S., Ma, R., Jin, S. H., Kang, Z., Huang, Y. and Rogers, J. A. (2013), "Multifunctional Epidermal Electronics Printed Directly Onto the Skin". Adv. Mater., 25: 2773-2778.*
Son et al., "Multifunctional wearable devices for diagnosis and therapy of movement disorders", Nature Nanotechnology, Mar. 30, 2014, vol. 9, pp. 397-404.*
Dae-Hyeong Kin, Nanshu Lu, Rui Ma, Yun-Soung Kim, Rak-Hwan Kim, Shuodao Wang, Jian Wu, Sang Min Won, Hu Tao, Ahmad Islam, Ki Jun Yu, Tae-Il Kim, Raeed Chowdhury, Ming Ying, Lizhi Su, Ming Li, Hyun-Joong Chung, Hohyun Keum, Martin McCormick, Ping Liu, Yong-Wei Zhang, Fiorenze G. Omenetoo, Yonggang Huang, Todd Coleman, John A. Rogers; Epidermal Electronics; www.sciengemag.org; Aug. 12, 2011, Corrected Sep. 23, 2011; vol. 333; pp. 838-843.
Woon-Hong Yeo, Yun-Soung Kim, Jongwoo Lee, Abid Ameen, Luke Shi, Ming Li, Shuodao Wang, Rui Ma, Sung Hun Jin, Zhan Kang, Yonggang Huang, and John A. Rogers; Multifunactional Epidermal Electronics Printed Directly Onto the Skin; Adv. Mater.; 2013; pp. 1-6.
Sheng Yu, Yihui Zhang, Lin Jia, Kyle E. Mathewson, Kyung-In Jang, Jeonghyun Kim, Haoran Fu, Xian Huang, Pranav Chava, Renhan Wang, Sanat Bhole, Lizhe Wang, Yoon Joo Na, Yue Guan, Matthew Sensors, Circuits, and Radios for the Skin; Science; Apr. 4, 2014; vol. 344; pp. 70-74.
Ming Ying, Andrew P. Bonifas, Nanshu Lu, Yewang Su, Rui Li, Huanyu Cheng, Abid Ameen, Yonggang Huang and John A. Rogers; Silicon nanomembranes for fingertip electronics; Nanotechnology; 2012; No. 23; pp. 1-11.
R. Chad Webb, Andrew P. Bonifas, Alex Behnaz, Yihui Zhang, Ki Jun Yu, Huanyu Cheng, Mingxing Shi, Zuguang Bian, Zhuangjian Liu, Yun-Soung Kim, Woon-Hong Yeo, Jae Suk Park, Jizhou Song, Yuhang Li, Yonggang Huang, Alexander M. Gorbach, and John A. Rogers; Ultrathin conformal devices for precise and continuous thermal characterization of human skin; Nature Materials; Oct. 2013; vol. 12; pp. 938-945, supplemental information pp. 1-27.
Donghee Son, Jongha Lee, Shutao Qiao, Roozbeh Ghaffari, Jaemin Kim, Ji Eun Lee, Changyeong Song, Seok Joo Kim, Dong Jun Lee, Samuel Woojoo Jun, Shixuan Yang, Minjoon Park, Jiho Shin, Kyungsik Do, Mincheol Lee, Kwanghun Kang, Cheol Seong Hwang, Nanshu Lu, Taeghwan Hyeon and Dae-Hyeong Kim; Multifunctional wearable devices for diagnosis and therapy of movement disorders; Nature Nanotechnology; Mar. 30, 2014; pp. 1-8.
Lei Sun, Guoxuan Qin, Jung-Hun Seo, George K. Celler, Weidong Zhou, and Zhenqiang Ma; 12-GHz Thin-Film Transistors on Transferrable Silicon Nanomembranes for High-Performance Flexible Electronics; small; 2010; vol. 6, No. 22; pp. 2553-2557.
F. Axisa, D. Brosteaux, E. De Leersnyder, F. Bossuyt, J. Vanfleteren, B. Hermans, R. Puers; Biomedical Strecthable Systems Using Mid Based Stretchable Electronics Technology; Proceedings of the 29th Annual International Conference on the IEEE EMBS Cite International, Lyon France; Aug. 23-26, 2007; pp. 5687-5690.
David Talbot and Kyanna Sutton; Making Stretchable Electronics; MIT Technology Review; 2014; v1.13.05.10; pp. 1-2.
Christoph Keplinger, Jeong-Yun Sun, Choon Chiang Foo, Philipp Rothemund, George M. Whitesides, Zhigang Suo; Stretchable, Transparent, Ionic Conductors; www.sciencemag.org; Aug. 30, 2013; vol. 341; pp. 984-987.
Giovanni A. Salvatore, Niko Munzenrieder, Thomas Kinkeldei, Luisa Petti, Christoph Zysset, Ivo Strebel, Lars Buthe and Gerhard

(56) References Cited

OTHER PUBLICATIONS

Troster; Wafer-scale design of lightweight and transparent electronics that wraps around hairs; Nature Communications; Jan. 7, 2014; p. 1.
Peripheral Neuropathy; The Journal of American Medical Association; Apr. 21, 2010; vol. 303, No. 15; p. 1.
PCT International Search Report; International App. No. PCT/US2015/060975; dated Feb. 29, 2016; pp. 1-3.
European Patent Office, Supplmementary European Search Report, Pursuant to Rule 62 EPC; App. No. EP 15861098; dated May 29, 2018; pp. 1-8.
Chinese State Intellectual Property Office, Notification of the First Office Action, App. No. 201580063269.7 (based on PCT App. No. PCT/US2015/060975); dated Sep. 3, 2019 (received by our Agent on Sep. 10, 2019); pp. 1-12 (machine translation provided).

\* cited by examiner

SYSTEMS TO MONITOR BODY PORTIONS FOR INJURY AFTER IMPACT

If an Application Data Sheet (ADS) has been filed on the filing date of this application, it is incorporated by reference herein. Any applications claimed on the ADS for priority under 35 U.S.C. §§ 119, 120, 121, or 365(c), and any and all parent, grandparent, great-grandparent, etc. applications of such applications, are also incorporated by reference, including any priority claims made in those applications and any material incorporated by reference, to the extent such subject matter is not inconsistent herewith.

CROSS-REFERENCE TO RELATED APPLICATIONS

The present application claims the benefit of the earliest available effective filing date(s) from the following listed application(s) (the "Priority Applications"), if any, listed below (e.g., claims earliest available priority dates for other than provisional patent applications or claims benefits under 35 USC § 119(e) for provisional patent applications, for any and all parent, grandparent, great-grandparent, etc. applications of the Priority Application(s)).

PRIORITY APPLICATIONS

None.

If the listings of applications provided above are inconsistent with the listings provided via an ADS, it is the intent of the Applicant to claim priority to each application that appears in the Domestic Benefit/National Stage Information section of the ADS and to each application that appears in the Priority Applications section of this application.

All subject matter of the Priority Applications and of any and all applications related to the Priority Applications by priority claims (directly or indirectly), including any priority claims made and subject matter incorporated by reference therein as of the filing date of the instant application, is incorporated herein by reference to the extent such subject matter is not inconsistent herewith.

SUMMARY

In an aspect, a device includes, but is not limited to, a deformable substrate comprising a conformable structure configured to conform to a skin surface of a body portion; a sensor assembly coupled to the deformable substrate, the sensor assembly configured to generate one or more sense signals based on detection of a physical impact to the body portion and based on detection of a physiological parameter of the body portion; circuitry operably coupled to the sensor assembly and configured to receive the one or more sense signals based on detection of a physical impact to the body portion and to determine whether the physical impact exceeds a threshold impact value, the circuitry configured to instruct the sensor assembly to detect one or more physiological parameters of the body portion when the physical impact exceeds the threshold impact value; and a reporting device operably coupled to the circuitry and configured to generate one or more communication signals based on instruction by the circuitry.

In an aspect, a device includes, but is not limited to, a deformable substrate integrated with a textile configured to interface with a body portion; a sensor assembly coupled to the deformable substrate, the sensor assembly configured to generate one or more sense signals based on detection of a physical impact to the body portion and based on detection of a physiological parameter of the body portion; circuitry operably coupled to the sensor assembly and configured to receive the one or more sense signals based on detection of a physical impact to the body portion and to determine whether the physical impact exceeds a threshold impact value, the circuitry configured to instruct the sensor assembly to detect one or more physiological parameters of the body portion when the physical impact exceeds the threshold impact value; and a reporting device operably coupled to the circuitry and configured to generate one or more communication signals based on instruction by the circuitry.

The foregoing summary is illustrative only and is not intended to be in any way limiting. In addition to the illustrative aspects, embodiments, and features described above, further aspects, embodiments, and features will become apparent by reference to the drawings and the following detailed description.

DETAILED DESCRIPTION

Figure 1:
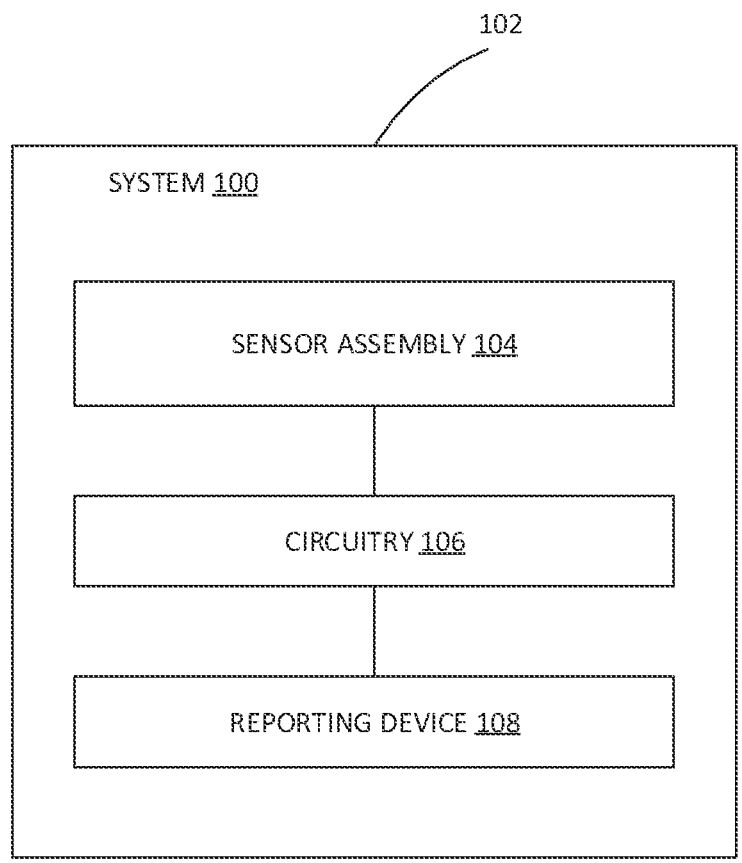
FIG. 1 is a schematic of a device for monitoring body portions for injury after a physical impact.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

Systems are described for monitoring body portions for injury, such as tissue and nerve damage, after a physical impact occurs to the body portion. Individuals afflicted with neuropathy (e.g., peripheral neuropathy) may have reduced capabilities to detect when a body portion comes in contact with another object or a surface due to an impairment of sensation, movement, or other normal body functions. Neuropathy can result from a disease, such as diabetes or immune system diseases, from interactions with various medications or medical treatments (such as chemotherapy), from inherited characteristics, from vitamin deficiency, from traumatic injury, from excessive alcohol usage, from infections (e.g., human immunodeficiency virus (HIV)), or other conditions and sources (see e.g., Torpy, Peripheral Neuropathy, JAMA, Vol. 303 (15), 1556 (April 2010), which is incorporated herein by reference). In an embodiment, the systems and devices described herein may be used to monitor for tissue damage after assessing whether a physical impact has occurred that exceeds a threshold impact value indicative of an impact to a body portion that may cause damage to the body portion. Once a physical impact is determined to exceed the threshold impact value, the device enables a physiological sensor to monitor one or more physiological conditions to determine whether an injury has occurred. The device can then report information associated with the physical impact to the body portion, the physiological condition of the body portion, a recommended course of action associated with treatment of the body portion, and so forth.

In embodiments, the systems and devices described herein employ a sensor assembly to monitor for a physical impact to a body portion and to generate one or more sense signals in response thereto. The sensors can include, but are not limited to, a pressure sensor, a proximity sensor, a strain sensor, and a motion sensor (e.g., an accelerometer). The systems described herein can include circuitry configured to receive the one or more sense signals from the sensor assembly associated with a physical impact to the body portion. The circuitry can be configured to determine whether the physical impact exceeds a threshold impact value and to instruct the sensor assembly to begin monitoring one or more physiological conditions of the body portion. For instance, in embodiments, the systems described herein employ a sensor assembly to monitor one or more physiological conditions of a subject following a physical impact and to generate one or more sense signals in response thereto. The sensors can include, but are not limited to, an oxygenation sensor, a temperature sensor, a pressure sensor, a chemical sensor, and an optical sensor.

In embodiments, the systems and devices described herein employ a reporting device configured to generate one or more communication signals based on instruction by the circuitry. The reporting device can convey various communications, including but not limited to, information associated with the physical impact to the body portion, information associated with the physiological condition of the body portion, information associated with a recommended course of action pertaining to treatment of the body portion, and so forth. In embodiments, the reporting device is configured to provide one or more of an auditory indication of the information, a visual indication of the information, and a tactile indication of the information.

In an embodiment, shown in FIG. 1, a system (or device) 100 is configured to monitor a body portion for injury following a physical impact, or after occurrence of one or more predetermined events, such as after an extremity with peripheral neuropathy has begun to move. The system 100 includes a substrate 102, a sensor assembly 104, circuitry 106, and a reporting device 108. In embodiments, the system 100 includes one or more epidermal electronic systems (EES) to monitor physiological, positional, and movement conditions for determining one or more of a physical impact to the body portion, a motion of the body portion, and a physiological condition of the body portion. EES describe classes of electronic systems that provide thicknesses, effective elastic moduli, and flexibility suitable for conforming to and interfacing with a skin surface (see, e.g., Kim et al., Epidermal Electronics, Science, Vol. 333, 838-843 (2011) and Yeo et al., Multifunctional Epidermal Electronics Printed Directly Onto the Skin, Advanced Materials Vol. 25(20), 2773-2778 (2013), which are incorporated herein by reference) and can incorporate sensors (e.g., physiological, temperature, strain) and associated circuitry (e.g., transistors, diodes, photodetectors, radio frequency components, capacitors, oscillators).

The substrate 102 is a deformable (e.g., flexible, stretchable) substrate configured to interface with, and conform to, a skin surface of a subject. The deformable and conformable nature of the substrate 102 facilitates interaction/interfacing with the skin surface, a generally low-modulus and deformable natural surface. For example, the substrate 102 can include one or more of an elastomeric polymer, a hydrocolloid film, a nanomembrane (e.g., silicon nanomembrane), or other deformable material. In embodiments, the substrate 102 can include one or more coating. The substrate 102 can be positioned in proximity with the skin surface according to various mechanisms including, but not limited to, affixed to the skin via an adhesive material, held in place by an external pressure, such as pressure provided by a material wrapped around the body portion (e.g., a fabric, a garment, etc.), and so forth. In embodiments, the substrate is integrated with a textile, described further herein with respect to FIGS. 8-10C. In embodiments, the substrate 102 is configured to reversibly deform to coordinate with a deformation of the skin surface of the body portion upon which the substrate 102 is mounted. For example, the substrate 102 can conform to the skin surface during a deformation of the skin surface, during a rest state of the skin surface, and so forth. In an embodiment, the substrate 102 includes a gas-permeable elastomeric sheet on which electronic components of an EES reside (see, e.g., Kim et al., incorporated herein by reference) configured to interface with a skin surface. In an embodiment, the substrate 102 includes a microfluidic enclosure defined by opposing structured elastomeric substrates between which electronic components of an EES reside (see e.g., Xu et al, Soft Microfluidic Assemblies of Sensors, Circuits, and Radios for the Skin, Science, Vol. 344, 70-74 (2014), which is incorporated herein by reference).

Figure 2:
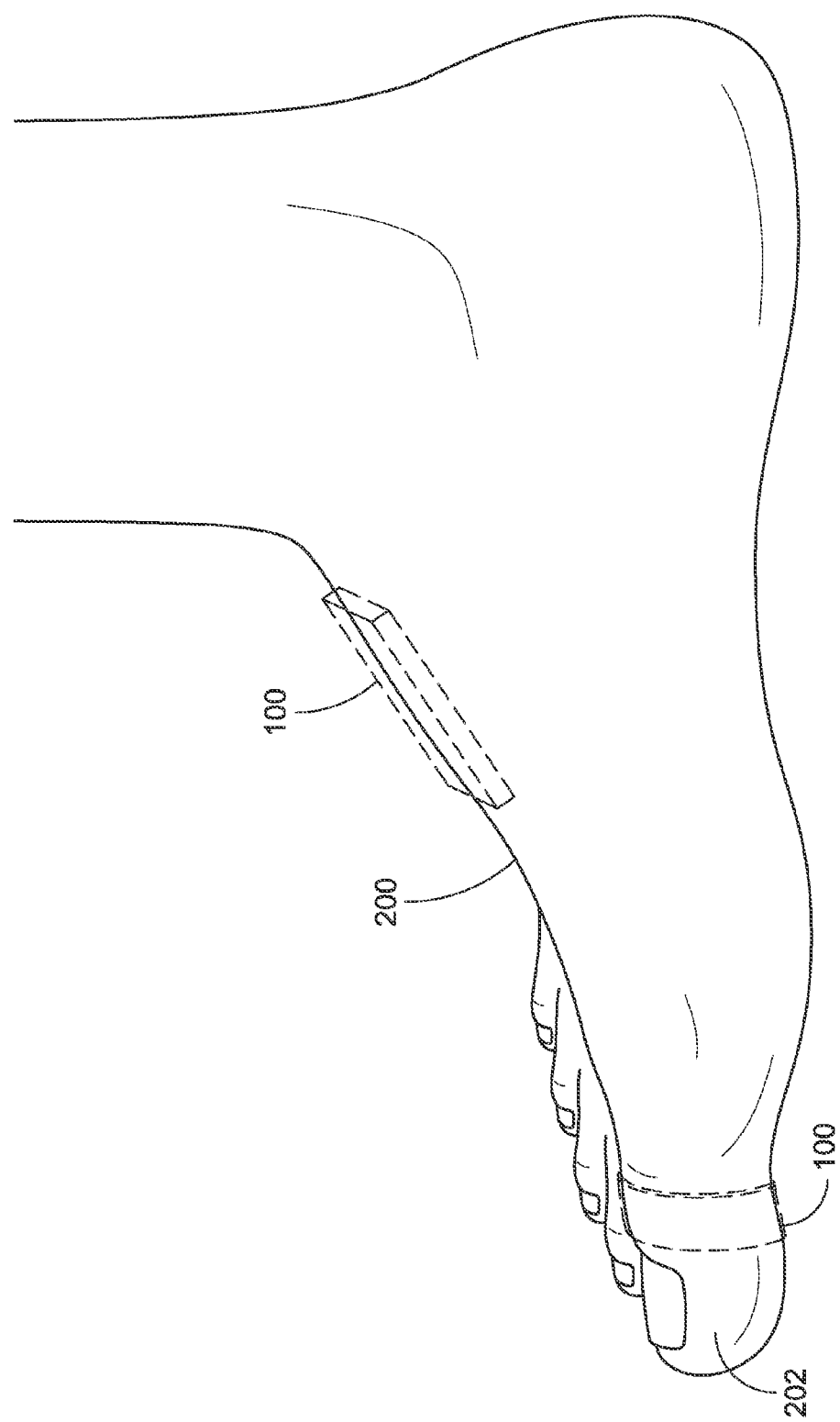
FIG. 2 is a schematic of an embodiment of a device such as shown in FIG. 1.

The substrate 102 can also be configured for interaction with a skin surface of a particular body portion. In example embodiments, the body portion includes one or more of a finger, a hand, a wrist, a toe, a foot, an ankle, an arm, an elbow, a leg, a knee, a shoulder, a hip, a spinal portion (e.g., a region proximate to one or more of a cervical spine, a thoracic spine, a lumbar spine, a sacral spine, and a coccygeal spine), a rib portion (e.g., a region proximate to a rib, such as where the rib attaches the spine), a torso, a neck, and a head region (e.g., face, scalp). For example, the substrate 102 can conform to or be formed as a tubular structure to facilitate interaction with a finger or toe, such as being wrapped around at least a portion of the finger or toe (see, e.g., Ying et al., Silicon nanomembranes for fingertip electronics, Nanotechnology, Vol. 23, No. 34, 1-7 (2012), which is incorporated herein by reference; Kim et al., ibid.; Yeo et al., ibid.). In an embodiment, shown in FIG. 2, the system 100 is positioned on a foot 200 of the subject for monitoring the foot 200 or other body portion in proximity to the foot 200 for injury (e.g., tissue damage, nerve damage, and so forth) following a physical impact to the foot 200. FIG. 2 also shows the system 100 wrapped around an individual toe 202 of the foot 200, where the system 100 can monitor the toe 202, such as one with diabetic neuropathy. In an implementation, the system 100 is associated with a patient afflicted with neuropathy, due to diabetes or other cause, where one or more devices 100 are configured to conform around each of one or more toes of the patient to monitor for physical impact to each respective toe and injuries associated with the impact.

In embodiments, the system 100 is configured to be disposable, such that the individual on which the system 100 is positioned (or other individual, such as a healthcare worker caring for the individual) can remove the system 100 for disposal and introduce a new system 100 for positioning on the body portion. In embodiments, the system 100 is reusable, such that after removing the system 100 from interaction with the body portion, the system 100 can be replaced on the same or different body portion for usage to monitor the body portion for physical impact and for injury following a physical impact.

The physical impact to the body portion can include an object falling on the foot, an interaction between the foot and an environmental surface (e.g., an impact between the foot and a floor surface or foreign object on a floor surface), and other impact-based interactions. Where an individual is affected by neuropathic condition, such as peripheral neuropathy, the individual may not recognize or feel that an impact has occurred to a particular body portion. The system 100 can be configured to monitor the body portion and report information to one or more of the individual, a healthcare professional, and a healthcare network, where the information can be one or more of information associated with physical impact to the body portion, information associated with a physiological condition of the body portion, and other information pertaining to the body portion.

Figure 3:
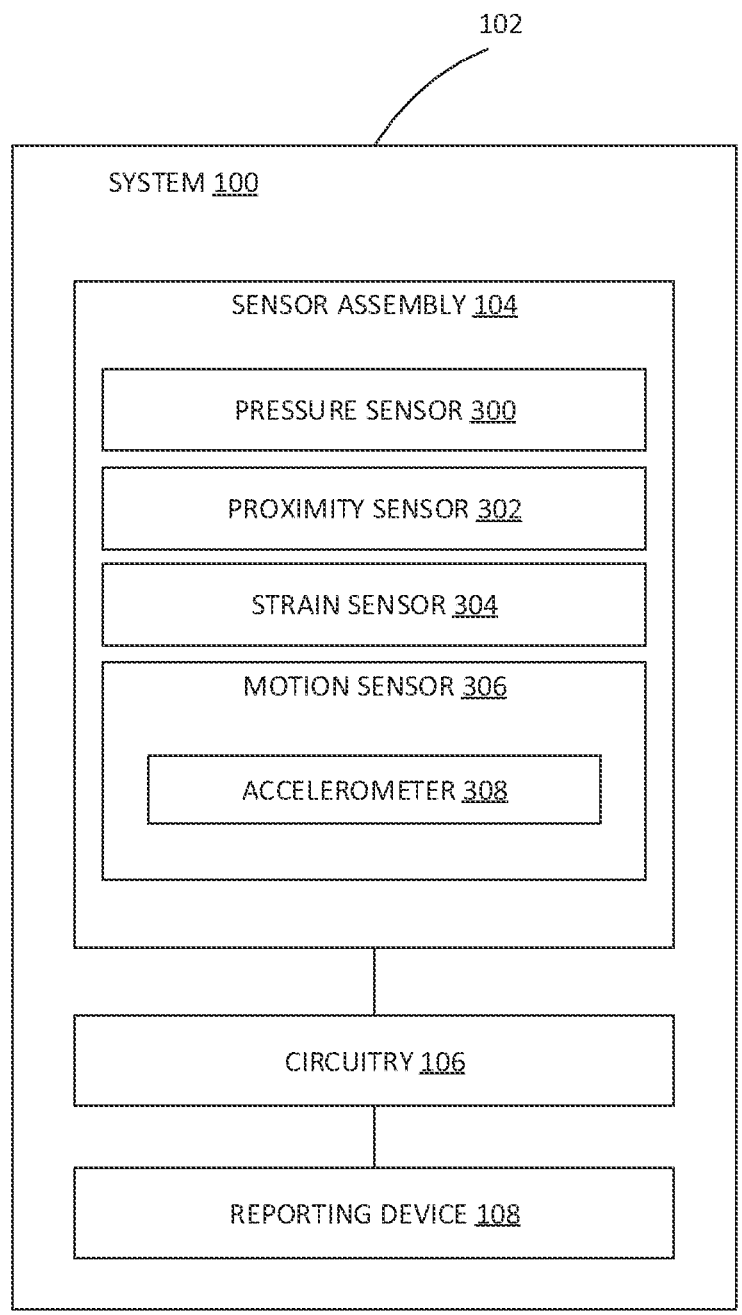
FIG. 3 is a schematic of an embodiment of a device such as shown in FIG. 1.

In embodiments, the sensor assembly 104 is configured to sense one or more conditions of the body portion to monitor for a physical impact to the body portion and to generate one or more sense signals in response thereto. The circuitry 106 (e.g., electric circuitry) is configured to receive the sense signals from the sensor assembly 104 for processing, such as to determine whether the sense signals are indicative of a physical impact, such as, for example, a physical impact of sufficient force to cause trauma to the body portion or a proximate body region. In embodiments, referring to FIG. 3, the sensor assembly 104 includes one or more of a pressure sensor 300, a proximity sensor 302, a strain sensor 304, and a motion sensor 306.

The pressure sensor 300 can be configured to measure a pressure imparted to a surface of the system 100, which can correlate to a pressure received by the body portion, such as for determinations regarding whether a physical impact exceeds a threshold impact value. In embodiments, the circuitry 106 is configured to instruct the sensor assembly 106 to detect one or more physiological parameters of the body portion based upon the one or more sense signals generated by the pressure sensor 300.

The proximity sensor 302 can include one or more of an infrared sensor and an optical sensor, each of which are configured to measure proximity (or a change in proximity over time) from the system 100 to another object or surface. For example, the proximity sensor 302 can measure a change in proximity over time between the system 100 (and corresponding body portion to which the system 100 is mounted) and the object or surface, where the absolute proximity, rate of change in proximity, relative change in proximity can be utilized to correlate to information related to a physical impact or an imminent impact between the body portion and the object or surface. In embodiments, the circuitry 106 is configured to instruct the sensor assembly 106 to detect one or more physiological parameters of the body portion based upon the one or more sense signals generated by the proximity sensor 302.

The strain sensor 304 can be configured to measure a strain or deformation of at least a portion of the system 100 or of the body portion to which the system 100 is mounted for determining whether the body portion has experienced a physical impact, particularly one which might cause traumatic injury to the body portion. For example, the strain sensor 304 may be a silicon nanomembrane-based sensor positioned over the skin surface to measure a strain-based physiological parameter (see, e.g., Son et al., Multifunctional wearable devices for diagnosis and therapy of movement disorders, Nature Nanotechnology, Vol. 9, 397-404 (2014), which is hereby incorporated by reference; Kim et al., ibid.; Yeo et al., ibid.). The strain sensor 304 can include stacked metallic materials to measure a strain, such as a titanium/gold stack (see, e.g., Salvatore et al., Wafer-scale design of lightweight and transparent electronics that wraps around hairs, Nature Communications, 5:2982 doi: 10.1038/ncomms3982 (2014)). In embodiments, the strain sensor 304 monitors the body portion for movement. For example, the strain sensor can measure a strain caused by deformation of the skin surface of the body portion to provide an indication of a movement of the body portion. In embodiments, the strain sensor 304 monitors deformation of the skin surface of the body portion during one or more of an impact to the body portion and swelling of the body portion. In embodiments, the circuitry 106 is configured to instruct the sensor assembly 106 to detect one or more physiological parameters of the body portion based upon the one or more sense signals generated by the strain sensor 304.

The motion sensor 306 is configured to detect one or more of a movement of the body portion and a position of the body portion. In embodiments, detection of the motion of the body portion is utilized as a trigger of when to begin monitoring for a physical impact to the body portion. The body portion can be the portion with which the system 100 interfaces or can be a portion proximate the portion with which the system 100 interfaces. In embodiments, the motion sensor 306 measures a speed of a movement, or relative change in speed of a movement of a body portion. For example, the system 100 can be positioned on an ankle of a subject and the motion sensor 306 measures the speed of movement of the ankle, such as one or more of a speed of movement during a flexing of the ankle during a walking motion, a speed of movement relative to a ground surface during a walking motion, or other movement. In embodiments, the motion sensor 306 includes an accelerometer 308 configured to measure one or more of motion of the body portion, vibration of the body portion, orientation of the body portion, and so forth. Such speed-based and acceleration-based measurements can be utilized as a reference measurement in determinations of when or whether a physical impact has occurred to the body portion. In embodiments, the accelerometer 308, either alone or in combination with a pressure or proximity sensor, is utilized to determine one or more conditions of a physical impact, including, but not limited to, a force of an impact and whether an impact has occurred. In embodiments, the motion sensor 306 is configured to measure the disposition of the body portion over a period of time. For example, the motion sensor 306 may measure a disposition of the body portion over time while the body portion is one or more of at rest, while in motion, and while held in a position that is not a rest position (e.g., tensed). In embodiments, the circuitry 106 is configured to instruct the sensor assembly 106 to detect one or more physiological parameters of the body portion based upon the one or more sense signals generated by the motion sensor 306.

Figure 4:
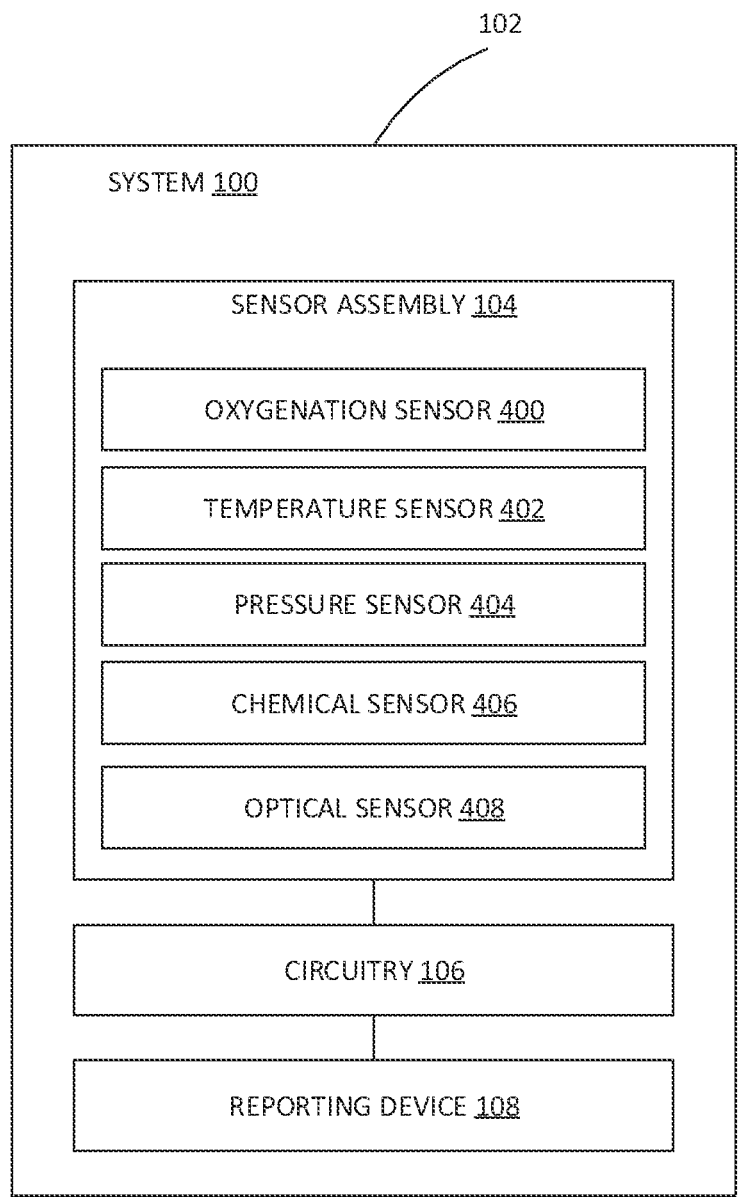
FIG. 4 is a schematic of an embodiment of a device such as shown in FIG. 1.

The sensor assembly 104 is configured to sense one or more physiological conditions of the body portion. In embodiments, the sensor assembly 104 begins to monitor one or more physiological conditions of the body portion after it has been determined (by the system 100, at a remote location, by a remote device, etc.) that a physical impact has occurred to the body portion. Such monitoring can provide insight as to whether the body portion, or a portion proximate the body portion, has sustained an injury from the physical impact. In embodiments, referring to FIG. 4, the sensor assembly 104 includes one or more of an oxygenation sensor 400, a temperature sensor 402, a pressure sensor 404, a chemical sensor 406, and an optical sensor 408. The sensor assembly 104 is configured to generate one or more sense signals responsive to monitoring for the one or more physiological conditions of the body portion. In embodiments, the circuitry 106 is configured to receive the one or more sense signals from the sensor assembly 104.

The oxygenation sensor 400 is configured to measure an oxygen analyte within the body portion, such as by measuring an oxygen concentration within a tissue, bloodstream, or other area of the body portion, which can be utilized to determine whether the body portion has sustained a traumatic injury. In embodiments, the oxygenation sensor 400 includes a pulse oximeter for a noninvasive measurement of oxygen concentration. The oxygenation sensor 400 is configured to generate one or more sense signals responsive to detection of an oxygen analyte, where the one or more sense signals are generally available for processing by the circuitry 106, or for reporting via the reporting device 108.

The temperature sensor 402 is configured to measure a localized or systemic temperature of the body portion, which can be utilized to determine whether the body portion has sustained a traumatic injury. For example, the temperature sensor can include, but is not limited to, a single point temperature sensor, a spatial imaging temperature sensor, and a microscale temperature sensor configured as a microscale heating element or actuator, such as one or more microscale temperature sensors incorporating thin serpentine features of thin metal or PIN diodes with nanoscale membranes (see, e.g., Webb et al., Ultrathin conformal devices for precise and continuous thermal characterization of human skin, Nature Materials, Vol. 12, 938-944 (2013), which is incorporated herein by reference). The temperature sensor 402 is configured to generate one or more sense signals responsive to detection of a temperature of the body portion, where the one or more sense signals are generally available for processing by the circuitry 106, or for reporting via the reporting device 108.

The pressure sensor 404 is configured to measure a pressure applied proximate to the system 100 located on the body portion, which can be utilized to determine whether the body portion has sustained a traumatic injury. For example, the pressure sensor 404 can be configured to measure a pressure imparted to a surface of the system 100, which can correlate to a pressure received by the body portion. The pressure measurements by the pressure sensor provide an indication regarding whether the body portion has sustained a physical injury or is likely to sustain a physical injury. The pressure sensor 404 is configured to generate one or more sense signals responsive to detection of a pressure applied to the body portion, where the one or more sense signals are generally available for processing by the circuitry 106, or for reporting via the reporting device 108. In embodiments, the pressure sensor 404 is configured to measure swelling of the body portion, such as, for example, swelling of a toe about which the system 100 is wrapped, distention of the skin against the pressure sensor 404, and so forth.

The chemical sensor 406 is configured to measure a chemical analyte within the body portion, such as by measuring an analyte concentration within a tissue, bloodstream, or other area of the body portion, which can be utilized to determine whether the body portion has sustained a traumatic injury. In embodiments, the chemical sensor 400 is configured to identify a component of blood, such as by measuring the presence of hemoglobin or other protein or related peptide, or cell component, by measuring a component of plasma, or by measuring a component of platelets. By measuring a component of blood, the chemical sensor 406 can be utilized to determine whether blood or other inflammatory fluid, or a component thereof, is present in the body portion outside of a blood vessel (artery, vein, capillary, etc.), or in an amount that is higher than normal in a specific area, which can indicate a traumatic injury to the body portion. The chemical sensor 406 is configured to generate one or more sense signals responsive to detection of a chemical analyte, where the one or more sense signals are generally available for processing by the circuitry 106, or for reporting via the reporting device 108.

The optical sensor 408 is configured to measure an optical property of the body portion, which can be utilized to determine whether the body portion has sustained a traumatic injury. In embodiments, the optical sensor 408 is configured to monitor the body portion for signs of discoloration (e.g., a deviation from a normal coloration of the body portion), which can provide an indication of rubor (such as that associated with inflammation or bruising), internal bleeding, or other condition indicative of a traumatic injury to the body portion. For example, the optical sensor can include, but is not limited to, a light-emitting diode, an LED coordinated with a photosensor, an imaging device, such as a camera, and so forth. The optical sensor 406 is configured to generate one or more sense signals responsive to detection of an optical property of the body portion, where the one or more sense signals are generally available for processing by the circuitry 106, or for reporting via the reporting device 108.

The circuitry 106 is configured to receive one or more sense signals from the sensor assembly 104 and to process the sense signals in order to provide control signals to portions of the system 100, such as to the reporting device 108. In embodiments, the circuitry 106 is a resident component that is coupled to the substrate 102. In embodiments, functionalities of the circuitry 106 can be performed remotely from the substrate 102, where the circuitry 106 can send and receive signals between a remote location (e.g., an external device) and the system 100 via associated wireless communication methods including, but not limited to acoustic communication signals, optical communication signals, radio communication signals, infrared communication signals, ultrasonic communication signals, and the like. The circuitry 106 can include a microprocessor, a central processing unit (CPU), a digital signal processor (DSP), an application-specific integrated circuit (ASIC), a field programmable gate entry (FPGA), or the like, or any combinations thereof, and can include discrete digital or analog circuit elements or electronics, or combinations thereof. In one embodiment, the computing device includes one or more ASICs having a plurality of predefined logic components. In one embodiment, the computing device includes one or more FPGAs having a plurality of programmable logic commands.

In embodiments, the circuitry 106 is operably coupled to the sensor assembly 104 and can receive one or more sense signals generated by the sensor assembly 104 for processing of the data associated therewith. The one or more sense signals from the sensor assembly can relate to detection of a physical impact to the body portion or to detection of physiological parameters of the body portion. In embodiments, the circuitry 106 is configured to receive one or more sense signals based on detection of a physical impact to the body portion from the sensor assembly 104 and to determine whether the physical impact exceeds a threshold impact value. For example, the threshold impact value can represent a force applied to a body portion at which the body portion has a statistical likelihood that a traumatic injury would occur to the body portion. In embodiments, the circuitry is configured to instruct the sensor assembly 104 to detect one or more physiological parameters of the body portion when it is determined that the physical impact to the body portion exceeds the threshold impact value.

Figure 5:
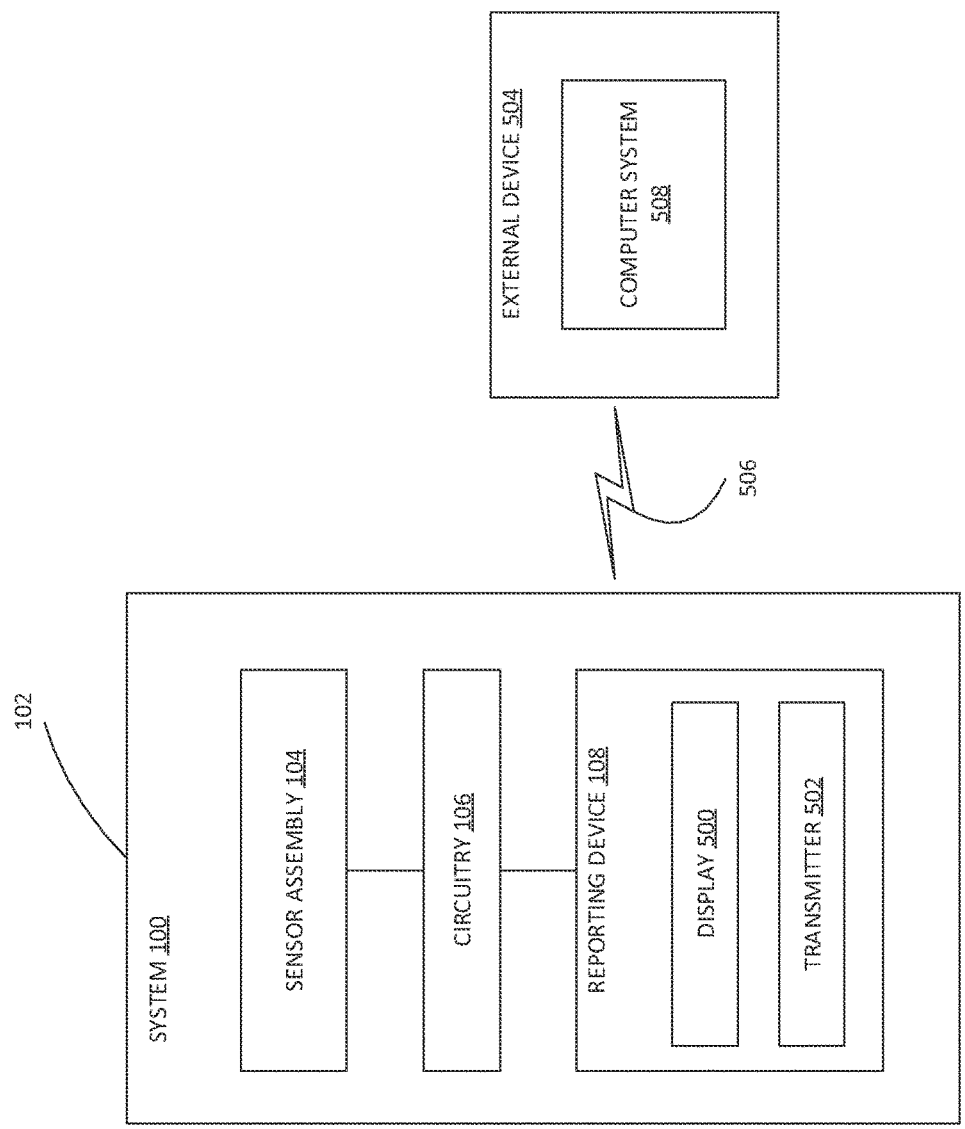
FIG. 5 is a schematic of an embodiment of a device such as shown in FIG. 1.

The reporting device 108 is configured to generate one or more communication signals to report information associated with operation of the system 100. In embodiments, the reporting device 108 is configured to generate one or more communication signals based on instruction by the circuitry 106. The information from the reporting device 108 may be provided one or more of visually (e.g., via transmission or display of visual information), audibly (e.g., via transmission or display of auditory information), and as data (e.g., via transmission or display of one or more data signals associated with the information to convey). The reporting device 108 may function in combination with the circuitry 106 to provide visual, auditory, or tactile information associated with detection of a physical impact to the body portion or with a physiological condition of the body portion (e.g., following a physical impact, such as an impact that exceeds a threshold impact value). In embodiments, such as shown in FIG. 5, the reporting device 108 includes a display 500 configured to report, communicate, or otherwise provide information to a user of the system 100. The display 500 may include, but is not limited to, a graphical user interface (GUI), a touchscreen assembly (e.g., a capacitive touch screen), a liquid crystal display (LCD), a light-emitting diode (LED) display, and a projection-based display. In embodiments, the reporting device 108 includes a transmitter 502 configured to transmit information from the system 100 to an external device 504 (e.g., a remote entity, a remote device, a remote server, a remote network, and so forth). In embodiments, the external device 504 includes a communication device, such as one or more of a mobile communication device and a computer system including, but not limited to, mobile computing devices (e.g., hand-held portable computers, Personal Digital Assistants (PDAs), laptop computers, netbook computers, tablet computers, and so forth), mobile telephone devices (e.g., cellular telephones and smartphones), devices that include functionalities associated with smartphones and tablet computers (e.g., phablets), portable game devices, portable media players, multimedia devices, satellite navigation devices (e.g., Global Positioning System (GPS) navigation devices), e-book reader devices (eReaders), Smart Television (TV) devices, surface computing devices (e.g., table top computers), Personal Computer (PC) devices, and other devices that employ touch-based human interfaces. The reporting device 108 can communicate (e.g., send and receive communication signals) with the external device 504 via one or more connected and wireless communication mechanisms (FIG. 5 displays a wireless communication mechanism 506) including, but not limited to acoustic communication signals, optical communication signals, radio communication signals, infrared communication signals, ultrasonic communication signals, and the like.

In embodiments, the external device 504 includes a computer system 508 configured to store and execute one or more computer-executable programs, whereby the reporter can interact with (e.g., remotely access, execute, and so forth) and modify the programs stored on or accessible by the computer system 508. For example, the circuitry 106 can direct the reporting device 108 to communicate with the computer system 508, such as to transmit to the computer system 508 one or more of data associated with detection of a physical impact, data associated with a determination that a physical impact has occurred, data associated with a comparison between data associated with detection of a physical impact and data associated with a threshold impact value, data associated with a physiological condition of the body portion, data associated with a physiological condition determined to relate to a traumatic injury to the body portion, data associated with a recommendation of a course of action following a determination of a physical impact, or other information associated with operation of the system 100. In embodiments, the external device 504 receives one or more communication signals from the reporting device 108 in order to process the data stored therein. For example, the external device 504 can process one or more of data associated with detection of a physical impact, data associated with a determination that a physical impact has occurred, data associated with a comparison between data associated with detection of a physical impact and data associated with a threshold impact value, data associated with a physiological condition of the body portion, data associated with a physiological condition determined to relate to a traumatic injury to the body portion, data associated with a recommendation of a course of action following a determination of a physical impact, or other information associated with operation of the system 100. In embodiments, the external device 504 is configured to process the data, to determine a recommended course of action based on the data, and to relay the recommended course of action to the reporting device 108. In embodiments, the recommended course of action includes a recommendation for medical treatment, such as when the data associated with the one or more physiological conditions provide an indication that the body portion has sustained a traumatic injury. The recommended course of action can also include a recommendation for continued monitoring of the body portion, such as to determine whether additional physical impacts occur, to determine whether the physiological conditions change over time (indicating an improvement in condition or indicating a deterioration in condition), and so forth. Other recommendations include, but are not limited to, a recommendation to cease monitoring of the body portion, a recommendation to begin monitoring the body portion, and a recommendation for performing a triage activity (e.g., applying a bandage, applying a tourniquet, applying heat, applying cold, applying pressure, elevating an appendage and so forth).

Figure 6:
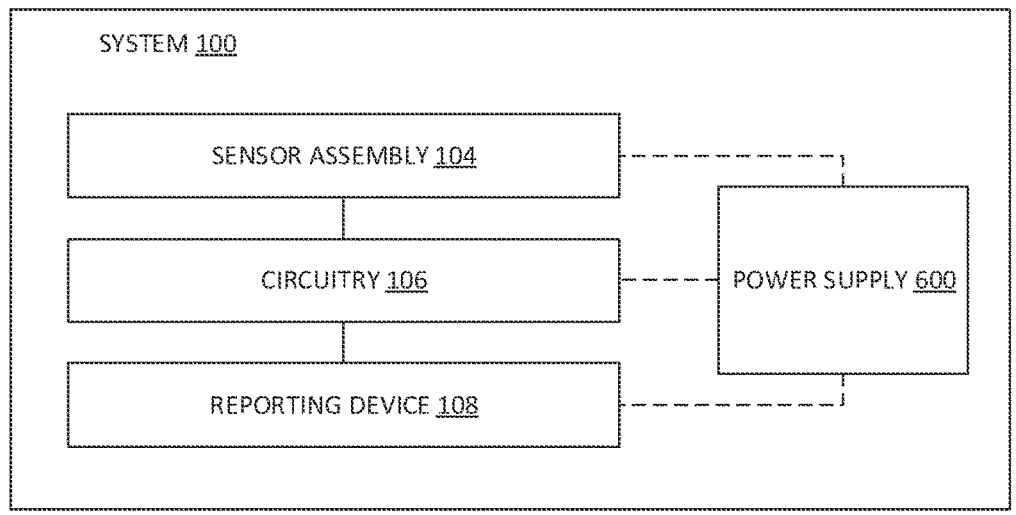
FIG. 6 is a schematic of an embodiment of a device such as shown in FIG. 1.

In embodiments, as shown in FIG. 6, the system 100 includes a power supply 600 configured to provide power to one or more components of the system 100 including, but not limited to, the sensor assembly 104, the circuitry 106, and the reporting device 108. In embodiments, the power supply 600 is a resident device component that is coupled to the substrate 102. Examples of resident device components include, but are not limited to, batteries (e.g., a thin film battery, a microbattery) and solar cells (e.g., silicon-based solar cells) configured to convert light energy into electrical energy for use by the components of the system 100. In embodiments, the power supply 600 includes one or more components positioned remotely from the substrate 102 that transmit power signals via associated wireless power methods including, but not limited to, inductive coupling of power signals. In such embodiments, the system 100 includes one or more components positioned on the substrate 102 configured to one or more of receive, process, and/or distribute the power signals that originate from components positioned remotely from the substrate 102. For example, the system 100 can include a wireless power coil coupled to the substrate 102 that is configured to receive a remote power signal, such as a remote power signal originating from a remote transmission coil (see, e.g., Kim et al., incorporated herein by reference).

Figure 7:
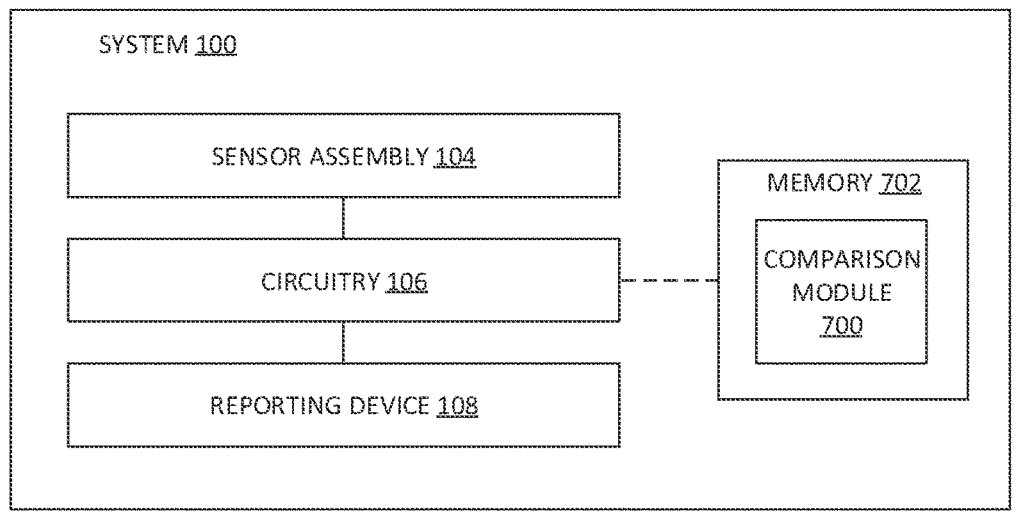
FIG. 7 is a schematic of an embodiment of a device such as shown in FIG. 1.

In embodiments, as shown in FIG. 7, the system 100 includes a comparison module 700 accessible by the circuitry 106 to compare one or more of data associated with a physical impact to the body portion detected by the sensor assembly 104 and data associated with a physiological condition of the body portion detected by the sensor assembly 104 to reference data indicative of a physical impact (e.g., a threshold impact value) and reference data indicative of an injury (e.g., a traumatic injury). In embodiments, the circuitry 106 accesses the comparison module 700 by accessing a computer memory 702, which can include, but is not limited to, random-access memory (RAM), read-only memory (ROM), electrically erasable programmable read-only memory (EEPROM), flash memory, or other memory technology, CD-ROM, digital versatile disks (DVD), or other optical disk storage, magnetic cassettes, magnetic tape, magnetic disk storage, or other magnetic storage devices, or any other medium which can be used to store the desired information maintained by the comparison module 700 and which can be accessed by the circuitry 106 or other associated accessing device. The reference data may be stored by the computer memory 702 of the system 100, can be accessible by the circuitry 106 via wireless means, or can be available to the circuitry 106 through another method, such as through a remote network, a cloud network, and so forth. The reference data may include physiological and biomechanical information pertaining to traumatic injuries and can include, but is not limited to, data associated with an oxygenation measurement or range of measurements indicative of a traumatic injury, a temperature measurement or range of measurements indicative of a traumatic injury, a pressure measurement or range of measurements indicative of a traumatic injury, a chemical analyte (e.g., a component of blood) measurement or range of measurements indicative of a traumatic injury, and an optical property (e.g., rubor) measurement or range of measurements indicative of a traumatic injury. By implementing the protocols of the comparison module 700, the circuitry 106 may compare the data obtained by the sensor assembly 104 pertaining to detection of a physical impact to the body portion to reference data indicative of a physical impact that exceeds a threshold impact value, where the threshold impact value is a value at which a statistical likelihood of injury or a risk of injury to the body portion has occurred or will occur. By implementing the protocols of the comparison module 700, the circuitry 106 may compare the data obtained by the sensor assembly 104 pertaining to physiological conditions of the body portion to reference data indicative of an injury to determine a statistical likelihood of injury or a risk of injury to the body portion has occurred or will occur, and to determine a recommended course of action based on the injury. The recommended course of action can include, but is not limited to, a recommendation to seek medical treatment, a recommendation for continued monitoring of the body portion, a recommendation to cease monitoring of the body portion, a recommendation to begin monitoring the body portion, and a recommendation for performing a triage activity (e.g., applying a bandage, applying a tourniquet, applying heat, applying cold, applying pressure, elevating an appendage, and so forth). In embodiments, the circuitry 106 further determines an action to be executed by the reporting device 108 based upon the comparison made between the data received from the sensor assembly 104 and the reference data. For example, where the circuitry 106 determines that the body portion is at a relatively high risk for incurring an injury, the circuitry 106 may control the reporting device 108 to take a first action (e.g., report a recommendation to seek immediate medical attention), whereas if the circuitry 106 determines that the body portion is at a lower risk for incurring an injury, the circuitry 106 may control the reporting device 108 to take a second action (e.g., provide a visible, audible, or tactile warning to the subject for continued monitoring).

Figure 8:
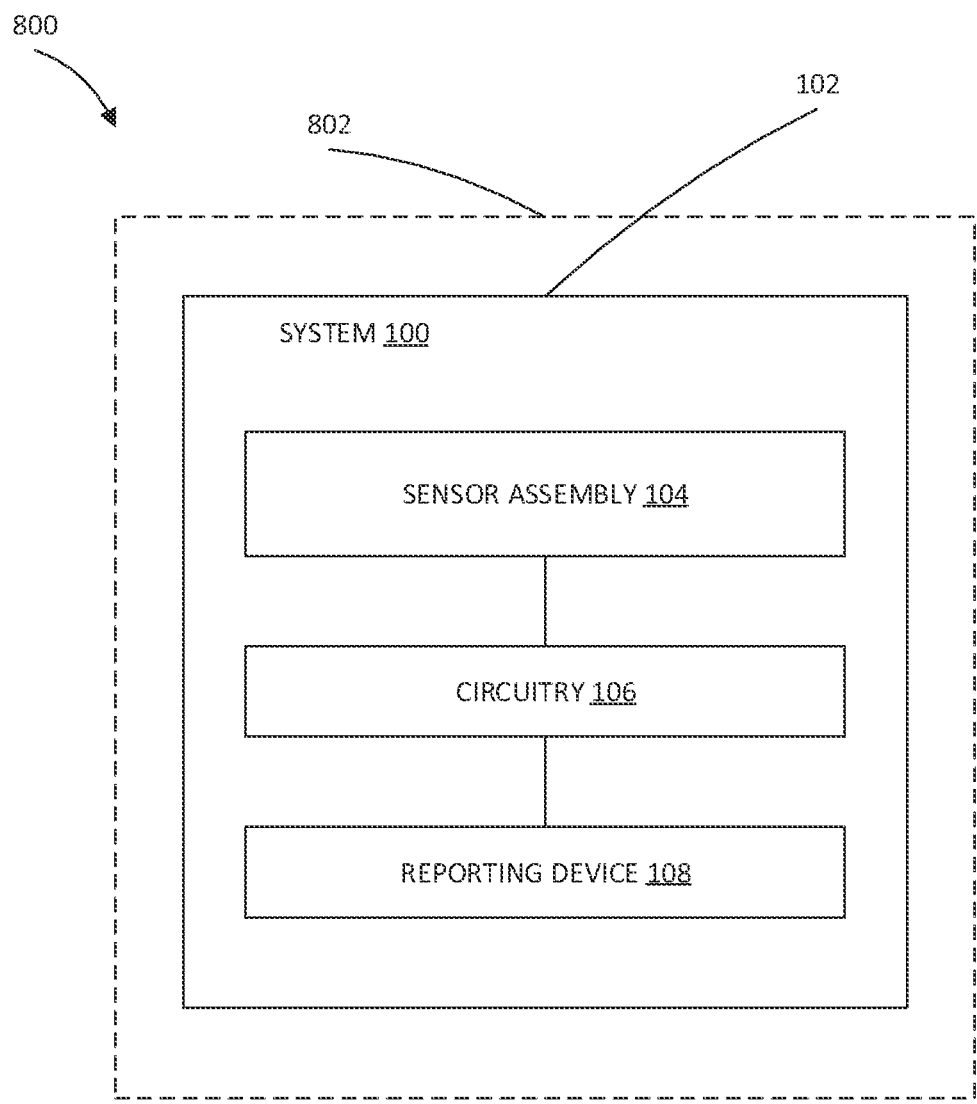
FIG. 8 is a schematic of a device for monitoring body portions for injury after a physical impact.
Figure 9:
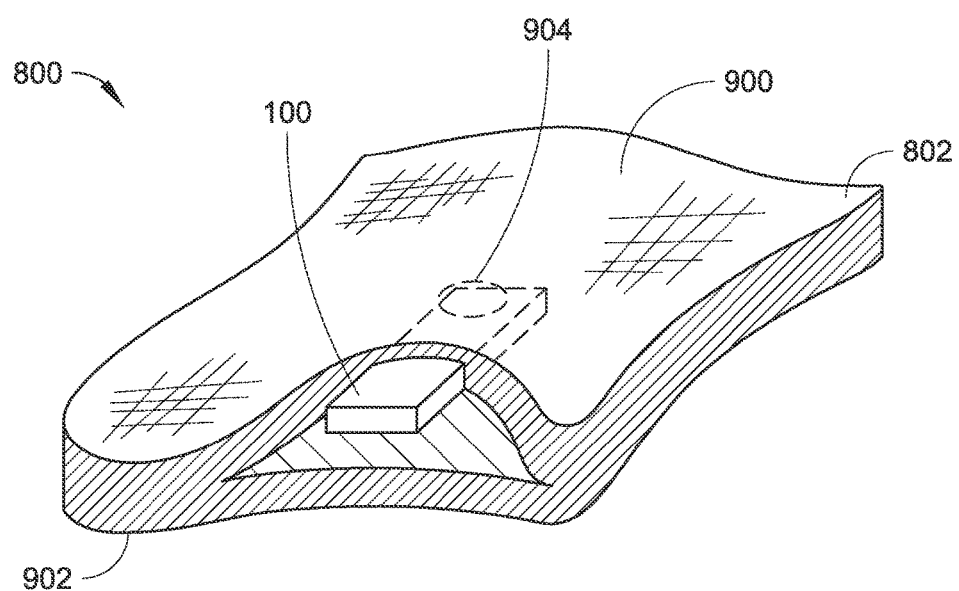
FIG. 9 is an isometric view of an embodiment of a device such as shown in FIG. 8.
Figure 10A:
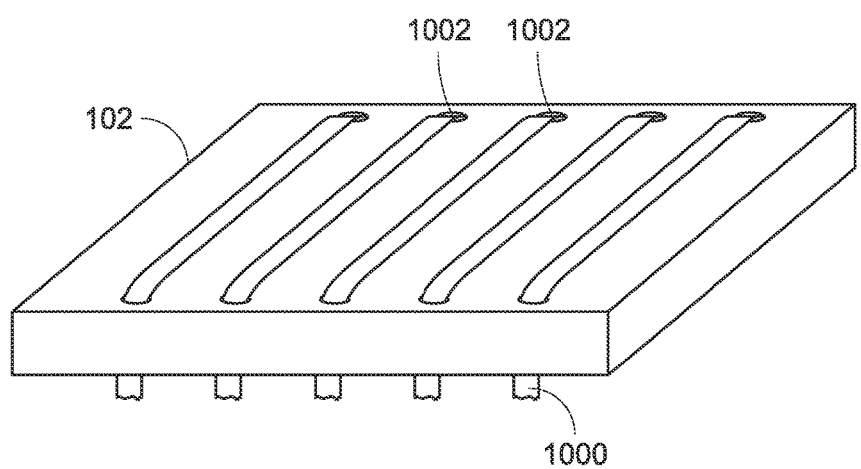
FIG. 10A is a diagrammatic isometric view of an embodiment of a device such as shown in FIG. 8.
Figure 10B:
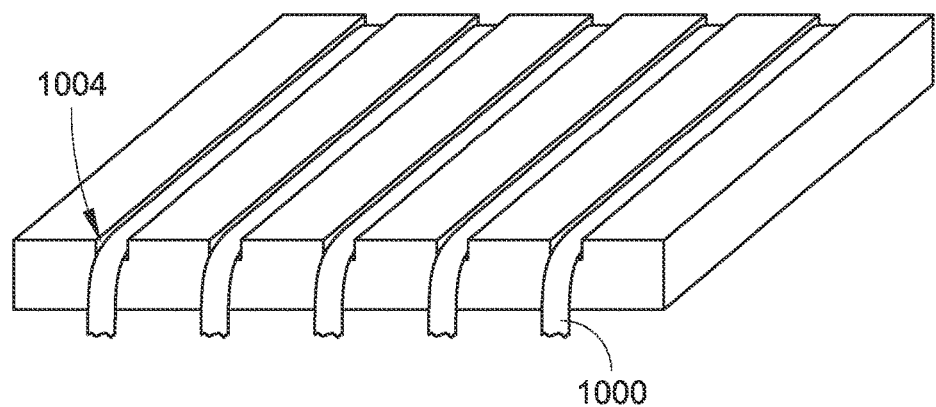
FIG. 10B is a diagrammatic side view of an embodiment of a device such as shown in FIG. 8.
Figure 10C:
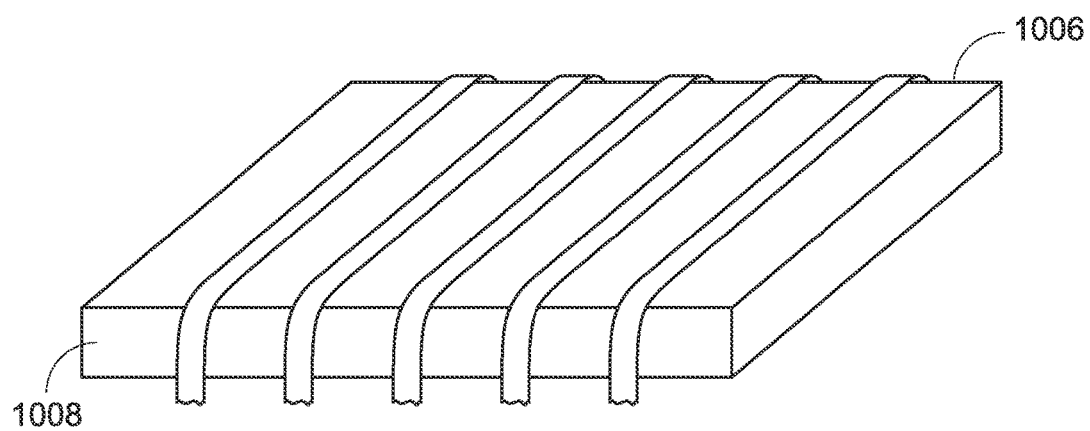
FIG. 10C is a diagrammatic side view of an embodiment of a device such as shown in FIG. 8.

FIG. 8 illustrates a device 800 for monitoring body portions for injury after a physical impact in accordance with example embodiments. The device 800 incorporates the system 100 integrated with a textile 802 to provide a supportive structure to interface with the body portion to monitor. For example, in embodiments the deformable substrate 102 is integrated with the textile 802, such that the textile 802 (including threading, weave patterns, and so forth) is configured to support the substrate 102 and corresponding components mounted thereto against the body portion when the textile 802 is positioned proximate to (e.g., wrapped around or about) the body portion. For example, in an embodiment, shown in FIG. 9, the textile 802 includes an inner surface 900 and an outer surface 902, wherein at least a portion of the deformable substrate is positioned between the inner surface 900 and the outer surface 902. The inner surface 900 can be configured to be adjacent the body portion when the textile 802 is positioned proximate to the body portion. In an embodiment, the inner surface 900 can define an aperture 904 through which the system 100 can have access to the body portion (e.g., for sensor assembly 104 measurements) when the textile 802 is positioned proximate to the body portion. In embodiments, the deformable substrate can be attached or mounted to the inner surface 900 or to the outer surface 902. The deformable substrate 102 can be attached via an adhesive material, via one or more threads of the textile 802, or other binding technique. In embodiments, the deformable substrate 102 is integral to a weave of the textile 802, whereby one or more fiber or thread of the textile can secure the substrate to or within the textile 802. For example, as shown in FIGS. 10A through 10O, the deformable substrate 102 can be integral to a weave of the textile 802 or bound to the textile 802 via interaction between one or more threads 1000 of the textile 802 with one or more corresponding apertures 1002 formed in the substrate 102 (shown in FIG. 10A), via interaction between one or more threads 1000 of the textile 802 with one or more corresponding channels or grooves 1002 formed by the substrate 102 (shown in FIG. 10B), via interaction between one or more threads 1000 of the textile 802 with one or more surfaces (e.g., top surface 1006, side surface 1008, and so forth) of the substrate 102 (shown in FIG. 10C), or via a combination of integrations. In embodiments, the textile 802 includes one or more electronic threads that incorporates one or more conductive materials (e.g., metallic, semi-conductive) to facilitate transfer of electric transmissions throughout at least a portion of the textile 802. The electronic threads can be integrated within a weave pattern of the textile 802, such that fabric threads are woven with electronic threads to form the textile 802.

In embodiments, the textile 802 is structured to conform to the body portion on which the device 800 is to be worn. For example, the textile 802 can be structured at least in part as a sleeve configured to interface with the body portion, such as an arm, wrist, elbow, leg, ankle, or knee. The textile 802 can be structured at least in part as a glove configured to interface with the body portion, such as a hand or a portion of a hand. The textile 802 can be structured at least in part as a sock configured to interface with the body portion, such as a foot or a portion of a foot. For example, the sock structure can be configured to conform to a portion of the foot, such as through a structure configured as a slipper-sock, a footie, a half-sock, and so forth. The textile 802 can be structured at least in part as a finger cot configured to interface with the body portion, such as a finger. The textile 802 can be structured at least in part as a finger warmer or finger protector, or toe warmer or to protector, configured to interface with the body portion, such as a finger or toe.

Figure 11:
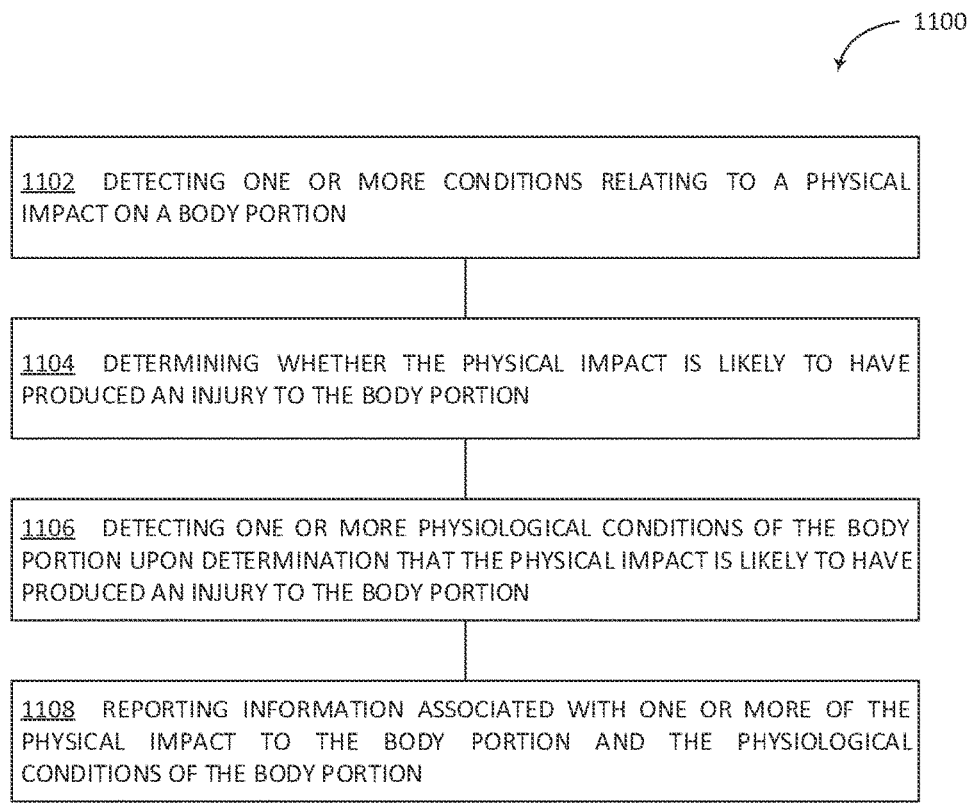
FIG. 11 is a flowchart of a method of monitoring body portions for injury after a physical impact.

FIG. 11 illustrates a method 1100 for monitoring body portions for injury after a physical impact in accordance with example embodiments. Method 1100 shows detecting one or more conditions relating to a physical impact on a body portion in block 1102. For example, the sensor assembly 104 can detect whether a physical impact has occurred with respect to a body portion, such as a body portion on which the system 100 is positioned. Method 1100 also includes determining whether the physical impact is likely to have produced an injury to the body portion in block 1104. For example, the circuitry 106 can receive one or more sense signals from the sensor assembly 104 relating to the detection of the physical impact and compare the sense signals to reference data, such as a threshold impact value, to determine whether the physical impact is likely to have produced an injury to the body portion. Method 1100 also includes detecting one or more physiological conditions of the body portion upon determination that the physical impact is likely to have produced an injury to the body portion in block 1106. Method 1100 further includes reporting information associated with one or more of the physical impact to the body portion and the physiological conditions of the body portion in block 1108. For example, the reporting device 108 can report (e.g., display, transmit) the reporting information associated with one or more of the physical impact to the body portion and the physiological conditions of the body portion.

The state of the art has progressed to the point where there is little distinction left between hardware, software, and/or firmware implementations of aspects of systems; the use of hardware, software, and/or firmware is generally (but not always, in that in certain contexts the choice between hardware and software can become significant) a design choice representing cost vs. efficiency tradeoffs. There are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation; or, yet again alternatively, the implementer may opt for some combination of hardware, software, and/or firmware. Hence, there are several possible vehicles by which the processes and/or devices and/or other technologies described herein can be effected, none of which is inherently superior to the other in that any vehicle to be utilized is a choice dependent upon the context in which the vehicle will be deployed and the specific concerns (e.g., speed, flexibility, or predictability) of the implementer, any of which may vary. Those skilled in the art will recognize that optical aspects of implementations will typically employ optically-oriented hardware, software, and or firmware.

In some implementations described herein, logic and similar implementations can include software or other control structures. Electronic circuitry, for example, may have one or more paths of electrical current constructed and arranged to implement various functions as described herein. In some implementations, one or more media can be configured to bear a device-detectable implementation when such media hold or transmit a device detectable instructions operable to perform as described herein. In some variants, for example, implementations can include an update or modification of existing software or firmware, or of gate arrays or programmable hardware, such as by performing a reception of or a transmission of one or more instructions in relation to one or more operations described herein. Alternatively or additionally, in some variants, an implementation can include special-purpose hardware, software, firmware components, and/or general-purpose components executing or otherwise invoking special-purpose components. Specifications or other implementations can be transmitted by one or more instances of tangible transmission media as described herein, optionally by packet transmission or otherwise by passing through distributed media at various times.

Alternatively or additionally, implementations may include executing a special-purpose instruction sequence or otherwise invoking circuitry for enabling, triggering, coordinating, requesting, or otherwise causing one or more occurrences of any functional operations described above. In some variants, operational or other logical descriptions herein may be expressed directly as source code and compiled or otherwise invoked as an executable instruction sequence. In some contexts, for example, C++ or other code sequences can be compiled directly or otherwise implemented in high-level descriptor languages (e.g., a logic-synthesizable language, a hardware description language, a hardware design simulation, and/or other such similar mode(s) of expression). Alternatively or additionally, some or all of the logical expression may be manifested as a Verilog-type hardware description or other circuitry model before physical implementation in hardware, especially for basic operations or timing-critical applications. Those skilled in the art will recognize how to obtain, configure, and optimize suitable transmission or computational elements, material supplies, actuators, or other common structures in light of these teachings.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein can be implemented via Application Specific Integrated Circuits (ASICs), Field Programmable Gate Arrays (FPGAs), digital signal processors (DSPs), or other integrated formats. However, some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, the mechanisms of the subject matter described herein are capable of being distributed as a program product in a variety of forms, and that an illustrative embodiment of the subject matter described herein applies regardless of the particular type of signal bearing medium used to actually carry out the distribution.

In a general sense, those skilled in the art will recognize that the various embodiments described herein can be implemented, individually and/or collectively, by various types of electro-mechanical systems having a wide range of electrical components such as hardware, software, firmware, and/or virtually any combination thereof and a wide range of components that may impart mechanical force or motion such as rigid bodies, spring or torsional bodies, hydraulics, electro-magnetically actuated devices, and/or virtually any combination thereof. Consequently, as used herein "electro-mechanical system" includes, but is not limited to, electrical circuitry operably coupled with a transducer (e.g., an actuator, a motor, a piezoelectric crystal, a Micro Electro Mechanical System (MEMS), etc.), electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of memory (e.g., random access, flash, read only, etc.)), electrical circuitry forming a communications device (e.g., a modem, communications switch, optical-electrical equipment, etc.), and/or any non-electrical analog thereto, such as optical or other analogs. Those skilled in the art will also appreciate that examples of electro-mechanical systems include but are not limited to a variety of consumer electronics systems, medical devices, as well as other systems such as motorized transport systems, factory automation systems, security systems, and/or communication/computing systems. Those skilled in the art will recognize that electro-mechanical as used herein is not necessarily limited to a system that has both electrical and mechanical actuation except as context may dictate otherwise.

In a general sense, the various aspects described herein can be implemented, individually and/or collectively, by a wide range of hardware, software, firmware, and/or any combination thereof and can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of memory (e.g., random access, flash, read only, etc.)), and/or electrical circuitry forming a communications device (e.g., a modem, communications switch, optical-electrical equipment, etc.). The subject matter described herein can be implemented in an analog or digital fashion or some combination thereof.

Those skilled in the art will recognize that at least a portion of the systems and/or processes described herein can be integrated into an image processing system. A typical image processing system generally includes one or more of a system unit housing, a video display device, memory such as volatile or non-volatile memory, processors such as microprocessors or digital signal processors, computational entities such as operating systems, drivers, applications programs, one or more interaction devices (e.g., a touch pad, a touch screen, an antenna, etc.), control systems including feedback loops and control motors (e.g., feedback for sensing lens position and/or velocity; control motors for moving/distorting lenses to give desired focuses). An image processing system can be implemented utilizing suitable commercially available components, such as those typically found in digital still systems and/or digital motion systems.

Those skilled in the art will recognize that at least a portion of the systems and/or processes described herein can be integrated into a data processing system. A data processing system generally includes one or more of a system unit housing, a video display device, memory such as volatile or non-volatile memory, processors such as microprocessors or digital signal processors, computational entities such as operating systems, drivers, graphical user interfaces, and applications programs, one or more interaction devices (e.g., a touch pad, a touch screen, an antenna, etc.), and/or control systems including feedback loops and control motors (e.g., feedback for sensing position and/or velocity; control motors for moving and/or adjusting components and/or quantities). A data processing system can be implemented utilizing suitable commercially available components, such as those typically found in data computing/communication and/or network computing/communication systems.

Those skilled in the art will recognize that at least a portion of the systems and/or processes described herein can be integrated into a mote system. Those having skill in the art will recognize that a typical mote system generally includes one or more memories such as volatile or non-volatile memories, processors such as microprocessors or digital signal processors, computational entities such as operating systems, user interfaces, drivers, sensors, actuators, applications programs, one or more interaction devices (e.g., an antenna USB ports, acoustic ports, etc.), control systems including feedback loops and control motors (e.g., feedback for sensing or estimating position and/or velocity; control motors for moving and/or adjusting components and/or quantities). A mote system may be implemented utilizing suitable components, such as those found in mote computing/communication systems. Specific examples of such components entail such as Intel Corporation's and/or Crossbow Corporation's mote components and supporting hardware, software, and/or firmware.

One skilled in the art will recognize that the herein described components (e.g., operations), devices, objects, and the discussion accompanying them are used as examples for the sake of conceptual clarity and that various configuration modifications are contemplated. Consequently, as used herein, the specific exemplars set forth and the accompanying discussion are intended to be representative of their more general classes. In general, use of any specific exemplar is intended to be representative of its class, and the non-inclusion of specific components (e.g., operations), devices, and objects should not be taken limiting.

With respect to the use of substantially any plural and/or singular terms herein, those having skill in the art can translate from the plural to the singular and/or from the singular to the plural as is appropriate to the context and/or application. The various singular/plural permutations are not expressly set forth herein for sake of clarity.

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "operably coupled to" each other such that the desired functionality is achieved, irrespective of architectures or intermedial components. Likewise, any two components so associated can also be viewed as being "operably connected," or "operably coupled," to each other to achieve the desired functionality, and any two components capable of being so associated can also be viewed as being "operably couplable," to each other to achieve the desired functionality. Specific examples of operably couplable include but are not limited to physically mateable and/or physically interacting components, and/or wirelessly interactable, and/or wirelessly interacting components, and/or logically interacting, and/or logically interactable components.

In some instances, one or more components can be referred to herein as "configured to," "configured by," "configurable to," "operable/operative to," "adapted/adaptable," "able to," "conformable/conformed to," etc. Those skilled in the art will recognize that such terms (e.g. "configured to") can generally encompass active-state components and/or inactive-state components and/or standby-state components, unless context requires otherwise.

While particular aspects of the present subject matter described herein have been shown and described, it will be apparent to those skilled in the art that, based upon the teachings herein, changes and modifications can be made without departing from the subject matter described herein and its broader aspects and, therefore, the appended claims are to encompass within their scope all such changes and modifications as are within the true spirit and scope of the subject matter described herein.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A device, comprising:
    a deformable substrate comprising a conformable structure configured to conform to a skin surface of a body portion;
    a sensor assembly coupled to the deformable substrate, the sensor assembly including
        a motion sensor configured to detect a movement of the body portion and to generate one or more sense signals responsive to the detection of the movement, a strain sensor configured to detect a deformation of the skin surface of the body portion and to generate one or more sense signals based on detection of a physical impact to the body portion via detection of the deformation of the skin surface by the strain sensor, and an optical sensor configured to detect one or more physiological parameters of the body portion including an optical property of the body portion and to generate one or more sense signals based on detection of the optical property of the body portion, the optical property of the body portion including at least one of a rubor property or a discoloration property;

circuitry operably coupled to the sensor assembly, the circuitry including circuitry configured to receive the one or more sense signals responsive to the detection of the movement, circuitry configured to instruct the sensor assembly to begin monitoring for the physical impact to the body portion based upon the received one or more sense signals responsive to the detection of the movement, circuitry configured to receive the one or more sense signals based on detection of a physical impact to the body portion, circuitry configured to determine whether the physical impact exceeds a threshold impact value, circuitry configured to instruct the sensor assembly to detect the physiological parameter of the body portion including the optical property of the body portion when the physical impact exceeds the threshold impact value, and circuitry configured to compare the optical property of the body portion to reference optical property data indicative of a traumatic injury; and a reporting device operably coupled to the circuitry and configured to generate one or more communication signals based on instruction by the circuitry.

2. The device of claim 1, wherein the circuitry includes a comparison module configured to compare the one or more sense signals based on detection of a physical impact to the body portion to reference data indicative of the threshold impact value.

3. The device of claim 2, wherein the reference data indicative of the threshold impact value correlates to a threshold for a traumatic injury.

4. The device of claim 1, wherein the sensor assembly includes a pressure sensor configured to detect the physical impact to the body portion and to generate one or more sense signals responsive to the detection of the physical impact.

5. The device of claim 4, wherein the circuitry is configured to instruct the sensor assembly to detect one or more physiological parameters of the body portion based upon the one or more sense signals generated by the pressure sensor.

6. The device of claim 1, wherein the motion sensor includes an accelerometer.

7. The device of claim 1, wherein the reporting device is configured to provide an auditory indication pertaining to the one or more sense signals based on detection of a physical impact to the body portion.

8. The device of claim 1, wherein the reporting device is configured to provide an auditory indication pertaining to the one or more physiological parameters of the body portion detected by the sensor assembly.

9. The device of claim 1, wherein the reporting device is configured to provide a visual indication pertaining to the one or more sense signals based on detection of a physical impact to the body portion.

10. The device of claim 1, wherein the reporting device is configured to provide a visual indication pertaining to the one or more physiological parameters of the body portion detected by the sensor assembly.

11. The device of claim 1, wherein the reporting device is configured to provide a tactile indication pertaining to the one or more sense signals based on detection of a physical impact to the body portion.

12. The device of claim 1, wherein the reporting device is configured to provide a tactile indication pertaining to the one or more physiological parameters of the body portion detected by the sensor assembly.

13. The device of claim 1, wherein the reporting device is configured to communicate with an external device.

14. The device of claim 13, wherein the reporting device is configured to wirelessly communicate with the external device.

15. The device of claim 1, wherein the reporting device is configured to communicate with an external network.

16. The device of claim 15, wherein the external network includes a health provider network.

17. The device of claim 1, wherein the circuitry is configured to determine a recommended course of action based on the one or more physiological parameters of the body portion detected by the sensor assembly.

18. The device of claim 17, wherein the recommended course of action includes a recommendation for medical treatment.

19. The device of claim 17, wherein the reporting device is configured to report the recommended course of action.

20. The device of claim 19, wherein the reporting device is configured to report the recommended course of action to an external device.

21. The device of claim 19, wherein the reporting device is configured to report the recommended course of action to an external network.

22. The device of claim 21, wherein the external network includes a health provider network.

23. The device of claim 19, wherein the reporting device is configured to display the recommended course of action on a display device.

24. The device of claim 23, wherein the display device includes a display screen coupled to the deformable substrate.

25. The device of claim 1, further including a power supply configured to supply power to one or more of the sensor assembly, the circuitry, and the reporting device.

26. The device of claim 25, wherein the power supply includes a battery coupled to the deformable substrate.

27. The device of claim 26, wherein the battery includes a thin film battery coupled to the deformable substrate.

28. The device of claim 26, wherein the battery includes a microbattery coupled to the deformable substrate.

29. The device of claim 25, wherein the power supply includes one or more wireless power coils configured to receive a remote power signal.

30. The device of claim 29, wherein the one or more wireless power coils includes one or more inductive coils configured to receive a remote power signal from a transmission coil.

31. The device of claim 25, wherein the power supply includes a solar cell coupled to the deformable substrate.

32. The device of claim 1, wherein the sensor assembly includes a proximity sensor, wherein the proximity sensor is configured to measure a change in proximity over time between at least a portion of the device and another object or surface, wherein at least one of an absolute proximity, a rate of change in proximity, or a relative change in proximity correlates to a physical impact or an imminent impact between the body portion and the another object or surface; and wherein the circuitry is configured to instruct the sensor assembly to detect the optical property of the body portion responsive to the correlated physical impact or imminent impact.

33. The device of claim 1, wherein the body portion includes a body portion affected by neuropathy.

34. A method, comprising:
   detecting, via a motion sensor of an epidermal electronic system (EES) located on a skin surface of a body portion of an individual, a movement of the body portion;
   subsequent to detecting movement of the body portion, detecting, via a strain sensor of the epidermal electronic system (EES) located on the skin surface of the body portion of the individual, a physical impact to the body portion and associated deformation of the skin surface caused by impact with another object or surface;
   generating one or more sense signals based on detection of the physical impact to the body portion;
   determining whether the detected physical impact exceeds a threshold impact value;
   when the detected physical impact is determined to exceed the threshold impact value, instructing an optical sensor to detect one or more physiological parameters of the body portion, the one or more physiological parameters including an optical property of the body portion;
   comparing the optical property of the body portion to reference optical property data indicative of a traumatic injury; and
   generating one or more communication signals based on at least one of detection of the physical impact, determining whether the detected physical impact exceeds a threshold impact value, the one or more physiological parameters of the body portion, and comparison of the optical property of the body portion to reference optical property data indicative of the traumatic injury.

35. The method of claim 34, wherein determining whether the detected physical impact exceeds a threshold impact value includes:
   comparing the one or more sense signals based on detection of the physical impact to reference data indicative of the threshold impact value.

36. The method of claim 35, wherein the reference data indicative of the threshold impact value correlates to a threshold for a traumatic injury.

37. The method of claim 34, wherein detecting, via an epidermal electronic system (EES) located on a body portion of an individual, a physical impact to the body portion includes:
   detecting the physical impact to the body portion with a pressure sensor.

38. The method of claim 37, wherein instructing an optical sensor to detect one or more physiological parameters of the body portion includes:
   instructing the optical sensor to detect one or more physiological parameters of the body portion based on detecting the physical impact to the body portion with the pressure sensor.

39. The method of claim 34, further including:
   transmitting the one or more communication signals to an external device.

40. The method of claim 34, further including:
   wirelessly transmitting the one or more communication signals to an external device.

41. The method of claim 34, further including:
   determining a recommended course of action based on the one or more physiological parameters of the body portion.

42. The method of claim 41, further including:
   reporting the recommended course of action to at least one of an external device and an external network.

43. The method of claim 41, further including:
   displaying the recommended course of action on a display device.

44. The method of claim 34, wherein generating one or more communication signals based on at least one of detection of the physical impact, determining whether the detected physical impact exceeds a threshold impact value, and the one or more physiological parameters of the body portion includes:
   providing at least one of an auditory indication, a visual indication, and a tactile indication, the at least one of an auditory indication, a visual indication, and a tactile indication pertaining to at least one of detection of the physical impact, determining whether the detected physical impact exceeds a threshold impact value, and the one or more physiological parameters of the body portion.

45. The method of claim 34, further including:
   detecting, via a proximity sensor, a change in proximity over time between at least a portion of the epidermal electronic system (EES) and the another object or surface, wherein at least one of an absolute proximity, a rate of change in proximity, or a relative change in proximity correlates to a physical impact or an imminent impact between the body portion and the another object or surface; and
   instructing the optical sensor to detect the optical property of the body portion responsive to the correlated physical impact or imminent impact.

46. The method of claim 34, wherein detecting, via a strain sensor of an epidermal electronic system (EES) located on a skin surface of a body portion of an individual, a physical impact to the body portion and associated deformation of the skin surface caused by impact with another object or surface includes:
   detecting, via a strain sensor of an epidermal electronic system (EES) located on a skin surface of a body portion of an individual affected by neuropathy, a physical impact to the body portion and associated deformation of the skin surface caused by impact with another object or surface.

47. The method of claim 34, wherein the reference optical property data includes at least one of a rubor measurement or a discoloration measurement.

48. A computer program product comprising:
   non-transitory computer-readable media having encoded instructions for executing a method for monitoring a biological body portion for injury following a physical impact, the method including:
      detecting, via a motion sensor of an epidermal electronic system (EES) located on a skin surface of a body portion of an individual, a movement of the body portion;
      subsequent to detecting movement of the body portion, detecting, via a strain sensor of the epidermal electronic system (EES) located on the skin surface of the body portion of the individual, a physical impact to the body portion and associated deformation of the skin surface caused by impact with another object or surface;

generating one or more sense signals based on detection of the physical impact to the body portion;

determining whether the detected physical impact exceeds a threshold impact value;

when the detected physical impact is determined to exceed the threshold impact value, instructing an optical sensor to detect one or more physiological parameters of the body portion, the one or more physiological parameters including an optical property of the body portion;

comparing the optical property of the body portion to reference optical property data indicative of a traumatic injury; and generating one or more communication signals based on at least one of detection of the physical impact, determining whether the detected physical impact exceeds a threshold impact value, the one or more physiological parameters of the body portion, and comparison of the optical property of the body portion to reference optical property data indicative of the traumatic injury.

* * * * *